United States Patent
Proulx et al.

(10) Patent No.: US 9,144,470 B2
(45) Date of Patent: Sep. 29, 2015

(54) TRACKING SYSTEM AND METHOD

(75) Inventors: Catherine Proulx, Verdun (CA); Louis-Philippe Amiot, Hampstead (CA); Yannick Boutin, Montréal (CA); Yonik Breton, Montréal (CA); Karine Duval, Montréal (CA); Benoit Pelletier, Laval (CA); Alain Richard, Lachine (CA); Myriam Valin, Laval (CA)

(73) Assignee: ORTHOSOFT INC., Montreal (CA)

( * ) Notice: Subject to any disclaimer, the term of this patent is extended or adjusted under 35 U.S.C. 154(b) by 954 days.

(21) Appl. No.: 12/410,854

(22) Filed: Mar. 25, 2009

(65) Prior Publication Data
US 2009/0247863 A1    Oct. 1, 2009

Related U.S. Application Data

(60) Provisional application No. 61/039,184, filed on Mar. 25, 2008, provisional application No. 61/100,173, filed on Sep. 25, 2008.

(51) Int. Cl.
*A61B 19/00* (2006.01)
*A61B 17/00* (2006.01)

(52) U.S. Cl.
CPC ... *A61B 19/5244* (2013.01); *A61B 2017/00115* (2013.01); *A61B 2017/00725* (2013.01); *A61B 2019/5248* (2013.01)

(58) Field of Classification Search
CPC .................. A61B 19/5244; A61B 2019/5248; A61B 2017/00725; A61B 2017/00115
USPC ............... 702/92–94, 150–153; 600/424, 426
See application file for complete search history.

(56) References Cited

U.S. PATENT DOCUMENTS

| 3,868,565 A | * | 2/1975 | Kuipers | .................. 324/207.26 |
| 5,971,976 A | | 10/1999 | Wang et al. | |
| 6,122,538 A | | 9/2000 | Sliwa et al. | |
| 6,786,877 B2 | | 9/2004 | Foxlin | |
| 7,065,393 B2 | | 6/2006 | Sati et al. | |
| 7,277,594 B2 | | 10/2007 | Hofstetter et al. | |

(Continued)

FOREIGN PATENT DOCUMENTS

| EP | 1 749 473 | 2/2007 |
| JP | H05-212056 A | 8/1993 |

(Continued)

OTHER PUBLICATIONS

I. Scott MacKenzie et al. "A Two-Ball Mouse Affords Three Degrees of Freedom", Late Breaking/Short Talks, CHI 97, Mar. 22-27, 1997, pp. 303-304.*

*Primary Examiner* — Alexander Satanovsky
(74) *Attorney, Agent, or Firm* — Norton Rose Fulbright Canada LLP (57) ABSTRACT

A tracking system is provided for tracking an objects. A first and a second trackable member each have an inertial sensor unit producing at least orientation-based data. A processing unit receives the orientation-based data from the trackable members. The processing unit has an orientation calculator calculating an orientation of the second trackable member with respect to the first trackable member from the orientation-based data of both said trackable members, whereby the processing unit calculates an orientation of the objects. A method is also provided.

8 Claims, 5 Drawing Sheets

(56) References Cited

U.S. PATENT DOCUMENTS

| | | |
|---|---|---|
| 2002/0103610 A1* | 8/2002 | Bachmann et al. ............ 702/94 |
| 2004/0039396 A1 | 2/2004 | Couture et al. |
| 2004/0243148 A1 | 12/2004 | Wasielewski |
| 2005/0113646 A1 | 5/2005 | Sotos et al. |
| 2006/0015018 A1* | 1/2006 | Jutras et al. .................. 600/301 |
| 2006/0058604 A1* | 3/2006 | Avinash et al. ............... 600/407 |
| 2007/0032723 A1 | 2/2007 | Glossop |
| 2007/0032748 A1 | 2/2007 | McNeil |
| 2007/0046525 A1* | 3/2007 | Holbrook et al. ............. 342/22 |
| 2007/0287901 A1 | 12/2007 | Strommer et al. |
| 2007/0287911 A1 | 12/2007 | Haid et al. |
| 2008/0051910 A1 | 2/2008 | Kammerzell et al. |
| 2008/0065084 A1 | 3/2008 | Couture et al. |
| 2009/0187120 A1* | 7/2009 | Nycz ............................. 600/587 |
| 2009/0300811 A1* | 12/2009 | Lundahl .............................. 2/15 |
| 2010/0016705 A1* | 1/2010 | Stone ............................ 600/407 |
| 2011/0031735 A1* | 2/2011 | Gerigk et al. .................. 283/70 |
| 2012/0074876 A1* | 3/2012 | Redler ............................ 318/41 |

FOREIGN PATENT DOCUMENTS

| | | |
|---|---|---|
| JP | 2002-090650 A | 3/2002 |
| WO | 2008/044679 A1 | 1/2008 |

* cited by examiner

TRACKING SYSTEM AND METHOD

CROSS-REFERENCE TO RELATED APPLICATIONS

This patent application claims priority on U.S. Provisional Patent Application No. 61/039,184, filed on Mar. 25, 2008, and U.S. Provisional Patent Application No. 61/100,173, filed on Sep. 25, 2008.

FIELD OF THE APPLICATION

The present application relates to tracking systems such as those used in computer-assisted surgery systems and, more particularly, to instrumentation used for the tracking of surgical tools during computer-assisted surgery and to a method for calibrating inertial sensors.

BACKGROUND OF THE ART

Tracking of surgical instruments or tools is an integral part of computer-assisted surgery (hereinafter CAS). The tools are tracked for position and/or orientation in such a way that information pertaining to bodily parts is obtained. The information is then used in various interventions (e.g., orthopedic surgery, neurological surgery) with respect to the body, such as bone alterations, implant positioning, incisions and the like during surgery.

The tracking systems may use different technologies, such as mechanical, acoustical, magnetic, optical and RF tracking. Depending on the technology used, different types of trackable members are fixed, permanently or temporarily, to the item that needs to be tracked. For instance, during Total Knee Replacement (TKR) surgery, trackable members are fixed to the limbs and to the different surgical instruments, and these trackable members are tracked by the tracking system. The CAS system calculates position and orientation data associated with the tracking, and the information displayed by the computer is used by the surgeon to visualize the position of the instrument(s) being manipulated with respect to the limbs, or in numerical values.

Two types of tracking systems are commonly used. The active tracking systems provide a transmitter as trackable member on the tool to be tracked, which transmitter emits signals to be received by a processor of the CAS system, which will calculate the position and/or orientation of the tool as a function of the signals received. The transmitters of the active tracking systems are powered, for instance by being wired to the CAS system or by being provided with an independent power source, so as to emit signals.

Passive tracking systems do not provide active transmitters on the tools as trackable members. The CAS system associated with passive tracking has an optical sensor apparatus provided to visually detect optical elements on the tools. The optical elements are passive, whereby no power source is associated therewith.

In order to obtain values for position and/or orientation, the optical elements must be in the line of sight of the optical sensor apparatus. Accordingly, with passive tracking systems, surgery takes place in a given orientation as a function of the required visibility between the optical sensor apparatus and the optical elements.

The trackable members currently used, whether active or passive, have a noticeable size depending on the technology used. For an electromagnetic system, a casing is wired to the CAS system and is secured to the instrument or to the patient. For an optical system, a trackable member generally comprises at least three optical elements. For instance, the optical elements are light sources wired to the CAS system and forming a scalene triangle. The light sources can be individually fixed or assembled on a base. In this second construction, the assembly is large and obstructive.

As an alternative, passive reflector spheres or patches can be used instead of light sources, and a light source is used to illuminate them (in the infrared spectrum).

Some factors must be considered when selecting a type of tracking system: the presence of wires in sterile zones for active trackable members; a line of sight required for navigation when using optical tracking; the size of the trackable members in order to deliver the required precision during surgery; the necessity for the surgeon to visualize a computer screen for intraoperative alignment information; the necessity for the surgeon to digitize landmarks on bones in order to build coordinate systems; the difficulty in integrating current optical, electromagnetic or radio-frequency sensors in disposable instruments (such as cutting guides) because of their volume.

SUMMARY OF THE APPLICATION

It is therefore an aim of the present application to provide a novel trackable member and tracking system.

It is a further aim of the present application that the tracking system be used in computer-assisted surgery.

Therefore, in accordance with the present application, there is provided a computer-assisted surgery system for tracking an instrument and a bone during surgery, comprising: a first trackable member having a first inertial sensor unit producing at least orientation-based data; and a second trackable member having a second inertial sensor unit producing at least orientation-based data, with one of the trackable members being connected to an instrument, and another of the trackable members being connected to a bone; and a processing unit for receiving the orientation-based data from the trackable members, the processing unit having an orientation calculator calculating an orientation of the second trackable member with respect to the first trackable member from the orientation-based data of both said trackable members, whereby the processing unit calculates an orientation of the instrument with respect to the bone.

Further in accordance with the present application, there is provided a method for tracking three degrees of freedom of orientation of an object, the method comprising: receiving orientation data for two degrees of freedom of orientation from an accelerometer-based reference tracking member affixed to the object; receiving orientation data for two degrees of freedom of orientation from an accelerometer-based calibration tracking member affixed to the object; determining angular rates of change of the reference tracking member and of the calibration tracking member while the object rotates about an axis of only one of the two degrees of freedom of orientation of the reference tracking member; and calibrating an orientation of the object with reference to the reference tracking member by using the determined angular rates of change to determine a third degree of freedom of orientation of the reference tracking member; whereby the object is trackable in three degrees of freedom of orientation.

Still further in accordance with the present application, there is provided a system for tracking three degrees of freedom of an orientation of an object, the system comprising: an accelerometer-based reference tracking member adapted to be affixed to the object, the reference tracking member producing orientation data for two degrees of freedom of orientation; an accelerometer-based calibration tracking member adapted to be affixed to the object, the calibration tracking member producing orientation data for two degrees of freedom of orientation; a processing unit for receiving the orientation data from the reference tracking member and the calibration tracking member, the processing unit comprising an orientation calculator for determining angular rates of change of the reference tracking member and the calibration tracking member while the object rotates about an axis of only one of the two degrees of freedom of the reference tracking member, and a calibration calculator for calibrating an orientation of the object with reference to the reference tracking member by using the determined angular rates of change to determine a third degree of freedom of orientation of the reference tracking member; whereby the object is trackable in three degrees of freedom of orientation.

DESCRIPTION OF THE PREFERRED EMBODIMENTS

Figure 1:
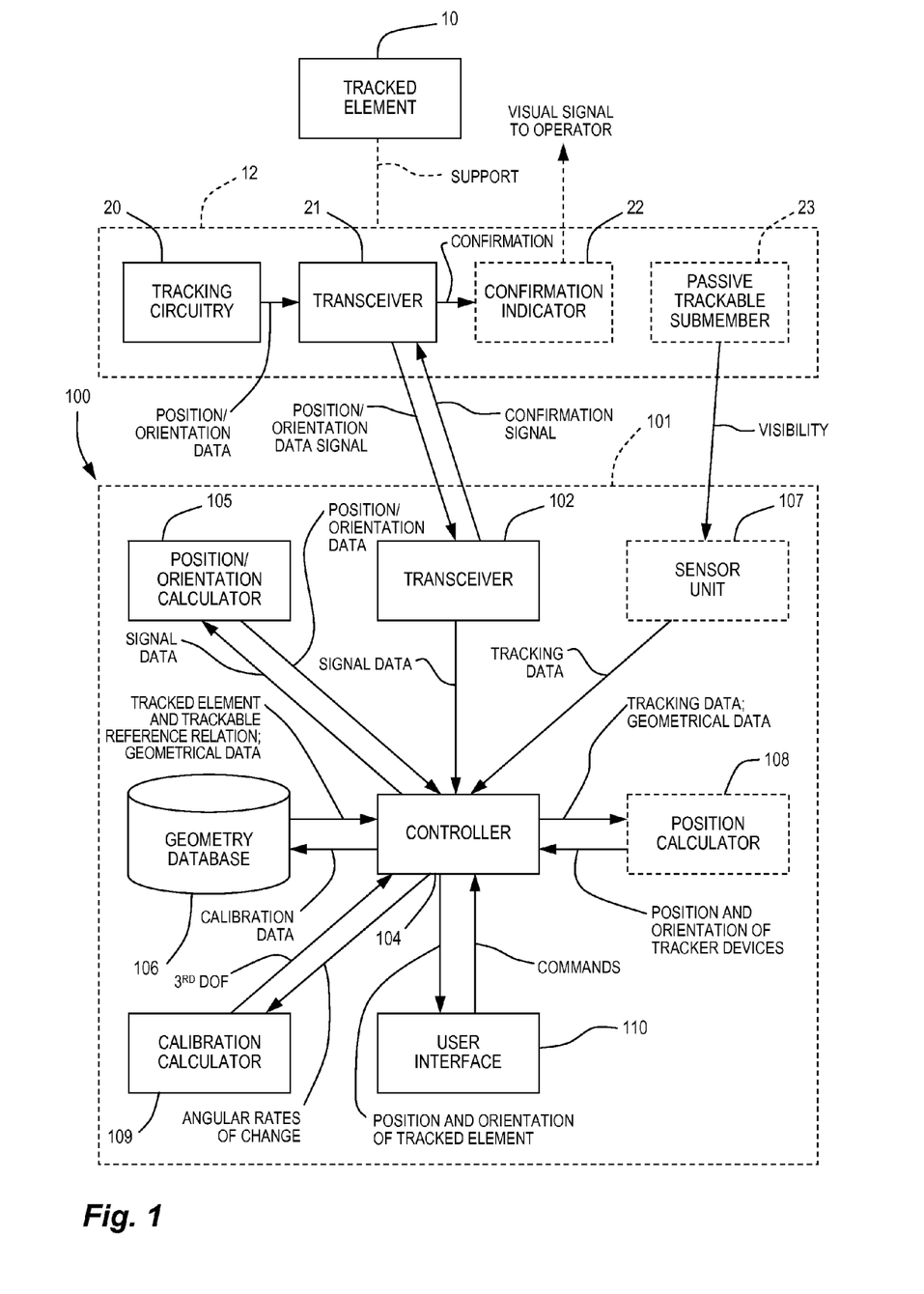
FIG. 1 is a block diagram of a tracking system in accordance with an embodiment of the present application.

Referring to FIG. 1, a MEMS (micro-electro-mechanical system) trackable member in accordance with an embodiment of the present application is generally shown at 12 as being fixed to a tracked element 10, such as a surgical tool, or a bodily element (e.g., bone). The MEMS trackable member 12 is used in a tracking system (such as a CAS tracking system) and comprises tracking circuitry 20 (i.e., inertial sensor unit), a transmitter 21 (or like communication circuitry, such as a wireless transmitter, a transceiver or the like), and optional confirmation indicator 22 and passive trackable submember 23. Reference to a transmitter will include a transceiver hereinafter, unless stated otherwise.

In an embodiment of the present disclosure, the tracking circuitry may be 6-degree-of-freedom (hereinafter DOF) micro-circuitry. The tracking circuitry 20 outputs data pertaining to the position and orientation of the trackable member 12.

Examples of suitable devices used as tracking circuitry 20 are the capacitive accelerometer sensor (CAPAS), electrolytic tilt sensors and the tri-axis sensor (TAS), amongst other possibilities. The CAPAS provides a 2-axis measurement of the acceleration (e.g., g force) of the tracked element 10 by being fixed thereto. In one embodiment, the physical size of the CAPAS is 7.4 by 7.0 by 3.5 mm.

A method and system are described hereinafter for the calibration of accelerometer-based tracking circuitry 20 for the accelerometer-based tracking circuitry 20 to provide 3 DOFS of orientation. In some applications, the tracking of 3 DOFs in orientation is sufficient—there is no need for the tracking circuitry 20 to be configured to provide more than the 3 DOFs in orientation, or to be connected to a passive trackable member providing the DOFs in position.

In the active state of the CAPAS, variations of the acceleration are reflective of a modification in the orientation of the CAPAS. The output of the CAPAS is a 2-axis relative angular value (or 3-axis if the CAPAS is calibrated). Therefore, the calibrated tracking circuitry 20 or the tracking circuitry 20 having two CAPAS in the aforementioned configuration provide real-time orientation data for the tracking circuitry 20, and thus for the tracked element 10.

In another embodiment, a trackable submember 23 may be provided as part of the trackable member 12, in order to provide position data related to the trackable member 12. Therefore, the orientation data output by the tracking circuitry 20 is combined with the position data obtained from the tracking of the trackable submember 23 to provide spatial position and orientation of the tracked element. For the trackable submember 23, known technologies such as ultrasound, optical elements and RF emitters can be used. In one embodiment, a retroreflective element (e.g., sphere, geometrical patch) is used. It is pointed out that a single trackable submember 23 (e.g., one sphere) is required as the trackable submember 23 is used to obtain position data. However, more than one trackable submember 23 can be used to increase the precision of the position data, or to increase the visibility of the trackable members 23, in the case of optical tracking. Therefore, with the use of CAPAS as tracking circuitry 20 with a single trackable submember 23, the trackable member 12 provides 6-DOF position and orientation in a compact device.

In another embodiment, a tri-axis accelerometer is used to provide position data for the trackable submember 23. By integrating the linear acceleration over time, the displacement from a known initial position can be computed to provide the current position of the submember 23.

As an alternative to CAPAS for the tacking circuitry 20, TAS provides position and orientation data. TAS consists of three gyroscopes and three accelerometers embedded in micro-circuitry. As an example, the physical size of available TAS is 23 by 32 by 5 mm. Therefore, using one of these TAS will provide position and orientation data as is the case with a combination of a pair of CAPAS and a trackable submember 23, but is larger than the latter combination.

The transmitter 21 is connected to the tracking circuitry 20 so as to transmit the tracking data of the tracking circuitry 20 to the processing system of the CAS system. The transmission of data may be wireless, or through wired connection. The technology used for the transmitter 21 may be selected to operate in a surgical environment, such as RF. As an example, Bluetooth™, Zigbee™ or Wi-Fi transmitters are considered for their wide availability and allow the integration of the trackable member 12 to surgical instruments. The trackable member 12 can be manufactured as a single disposable unit, possibly integrated to implant instrumentation (e.g. a disposable, self-trackable cutting guide for TKR). As an alternative embodiment, sensors can be configured to communicate necessary information between themselves.

Another feature considered for the trackable member 12 is the confirmation indicator 22 that provides data to the operator or surgeon. For instance, indications about a suitable position/orientation of the surgical tool may be provided directly on the tool, so as to facilitate the procedure for the surgeon/operator handling the tool. The confirmation indicator 22 is circuitry with on/off LEDs (e.g., red and a green LEDs) or another suitable form of compact electronic display responsive to signals or commands received from the CAS system. In the embodiment in which the trackable device 12 uses a confirmation indicator 22, the transmitter 21 is a transceiver that receives signals from the processing system of the CAS system. The confirmation indicator 22 is connected to the circuitry of the transceiver to receive signals and convert them to the visual signal provided to the operator/surgeon.

Another embodiment of the confirmation indicator 22 involves a series of LEDs or another suitable form of compact electronic display that would be turned on according to the position and orientation of the instrument upon which the trackable member 12 is fixed. This would allow communication of alignment/position information of the various surgical instruments as the surgeon/operator is manipulating them, in order to free the surgeon from having to look at the computer screen for equivalent information.

Amongst the surgical tools being used as tracked elements 10 are registration pointers, cutting blocks, drills, rasps, writing sticks and the like.

In order to calibrate the tracked element 10 having the trackable member 12 in the event that the tracked element 10 is a surgical instrument, the tip of the instrument is abutted against a reference point (calibration marker) to allow the CAS system to track the orientation of the instrument. Other types of calibration can also be used with the trackable member 12 For instance, a method is described hereinafter for calibrating an orientation of the tracked element 10 with reference to FIG. 5.

Still referring to FIG. 1, a tracking system incorporating the trackable member 12 is generally illustrated at 100, and is used with one or more of the trackable member 12. The tracking system may be a computer-assisted surgery system (CAS system), and has a processing unit 101, which typically comprises a computer having a processor. A receiver 102 is provided in the processing unit 101 so as to receive the position/orientation data signal from the trackable member 12. In the embodiment in which the trackable member 12 has a confirmation indicator 22, the receiver 201 is a transceiver sending confirmation signals to the trackable member 12.

A controller 104 is connected to the receiver 102. Therefore, the controller 104 receives the signal data from the receiver 102.

A position/orientation calculator 105 is used to convert the signal data received from the receiver/transmitter 102 into position/orientation data for the trackable member 12. More specifically, if the tracking circuitry 20 is a combination of CAPAS or a calibrated CAPAS, the signal data will be converted to an orientation of the trackable member 12. If the tracking circuitry 20 is a TAS, the signal data will be converted to a position and an orientation of the trackable member 12.

A geometry database 106 is provided so as to store the calibration data, and other intraoperative data such as bone models defined using registration pointers, for given CAS applications, axes and coordinate systems of objects. The calibration data is therefore a relation between the tracked element 10 and the trackable member 12, when position data is required for the application. In the embodiment in which a trackable submember 23 is used, the calibration data comprises geometrical data relating the trackable submember 23 to the tracked element 10.

Therefore, in an application requiring position data, the controller 104 receives the position/orientation data from the position/orientation calculator 105, and calculates position/orientation of the tracked element 10 using the relation data provided by the database 106. Accordingly, the controller 104 outputs position/orientation data to the user interface 110.

The processing unit 101 optionally has a sensor unit 107 (e.g., optical sensor apparatus) provided in order to track the trackable submember 23 of the trackable member 12, in the embodiment in which the trackable submember 23 is used in combination with a pair of CAPAS, or a calibrated CAPAS. Typically, the sensor unit 102 involves a pair of sensors (e.g., Navitrack™).

A position calculator 108 may be provided in association with the controller 104. The position calculator 108 receives the tracking data from the controller 104, which tracking data is obtained from the tracking by the sensor unit 107. With the geometrical data provided by the database 106, the position calculator 108 calculates the position of the tracked element 10.

The position of the tracked element 10 is sent to the controller 104 and is combined with the orientation of the tracked element 10, whereby the controller 104 produces positioned and orientation of the tracked element 10.

The tracking system 10 may be provided with a calibration calculator 109. The calibration calculator 109 is used with a pair of 2 DOF orientation trackable members 12 (e.g., CAPAS) as illustrated in FIGS. 3 and 4, and calibrates one of the trackable members 12 such that a third DOF in orientation is known and trackable.

This information is sent to the user interface 110, such that the user of the system 100 obtains information pertaining to the position and orientation of the tracked element in the various forms known to computer-assisted surgery (e.g., visual representation, numerical values such as angles, distances, etc.). It is pointed out that the database 106 may as well be part of the controller 104.

Figure 2:
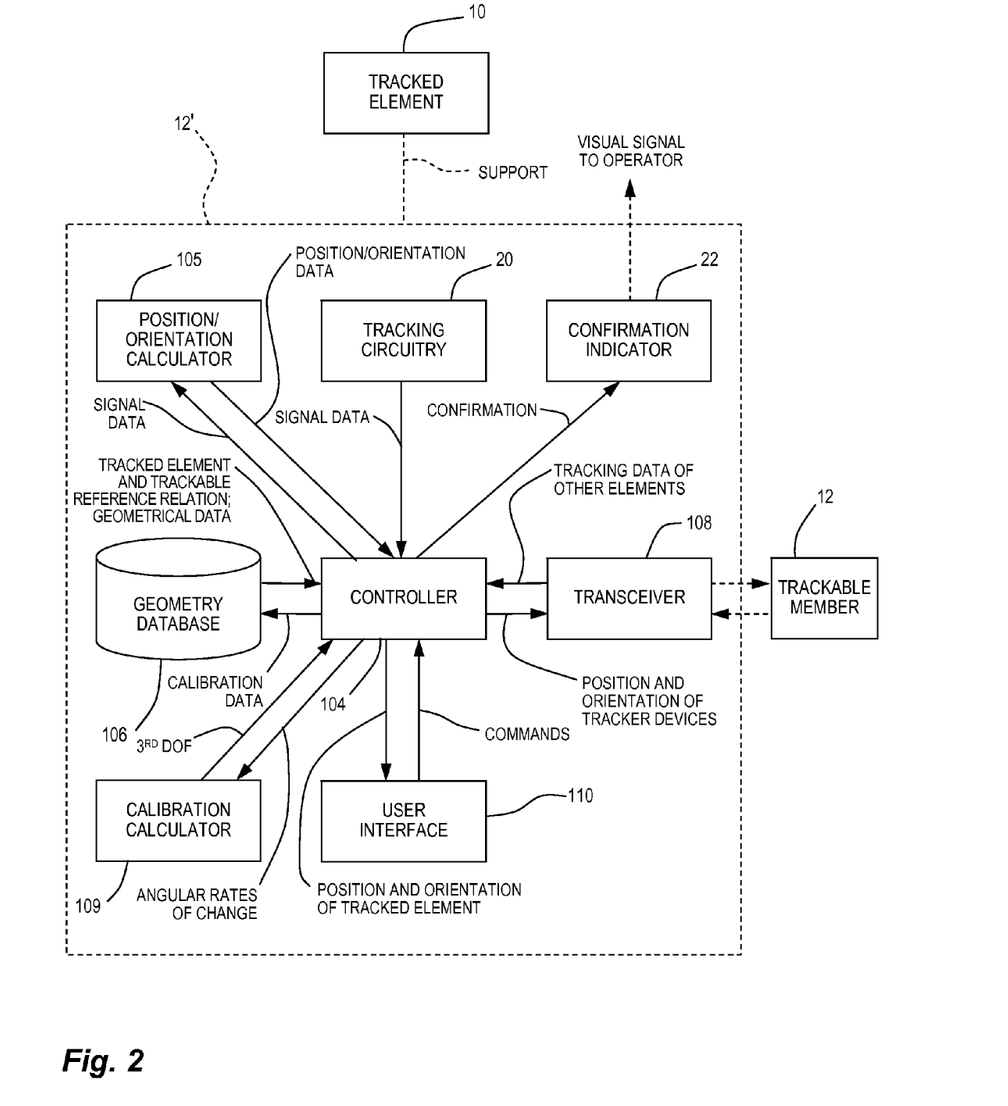
FIG. 2 is a block diagram of a self-enclosed tracking system in accordance with another embodiment of the present application.

Referring to FIG. 2, there is illustrated at 12' an embodiment of the trackable member in which a self-enclosed processing unit is connected to the tracked element 10. The trackable member 12' has the tracking circuitry 20, transceiver 21 and the confirmation indicator 22 described above for the trackable member 12, but also the controller 104, the position/orientation calculator 105, the geometry database 106, the calibration calculator 109 and the user interface 110, all in a compact self-enclosed casing secured directly to the tracked element 10. Accordingly, the transceiver 21 is used to share information with other trackable members 12' used concurrently during the surgical procedure.

Figure 3:
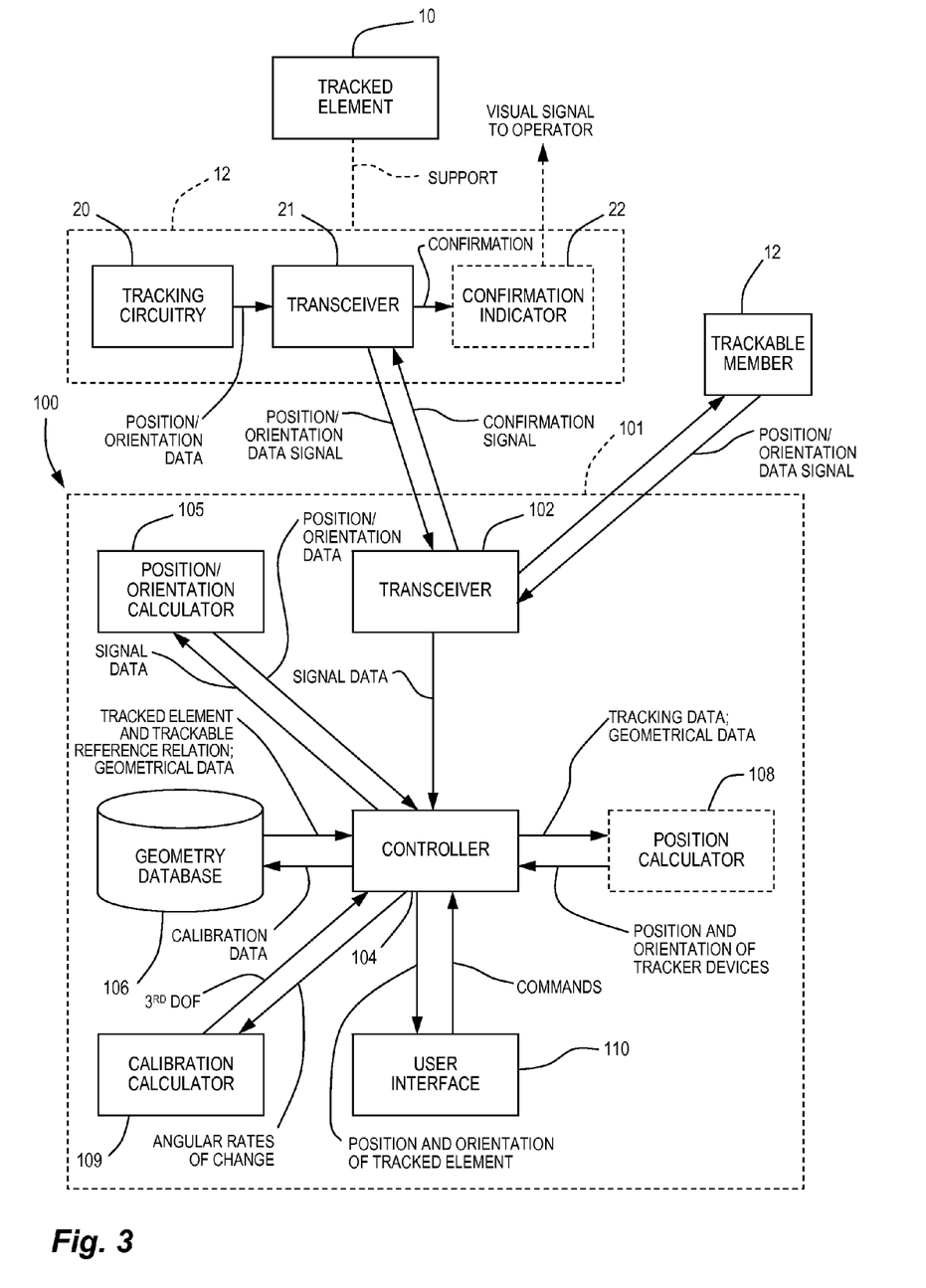
FIG. 3 is a block diagram of a tracking system in accordance with another embodiment of the present application, tracking a pair of trackable members.
Figure 4:
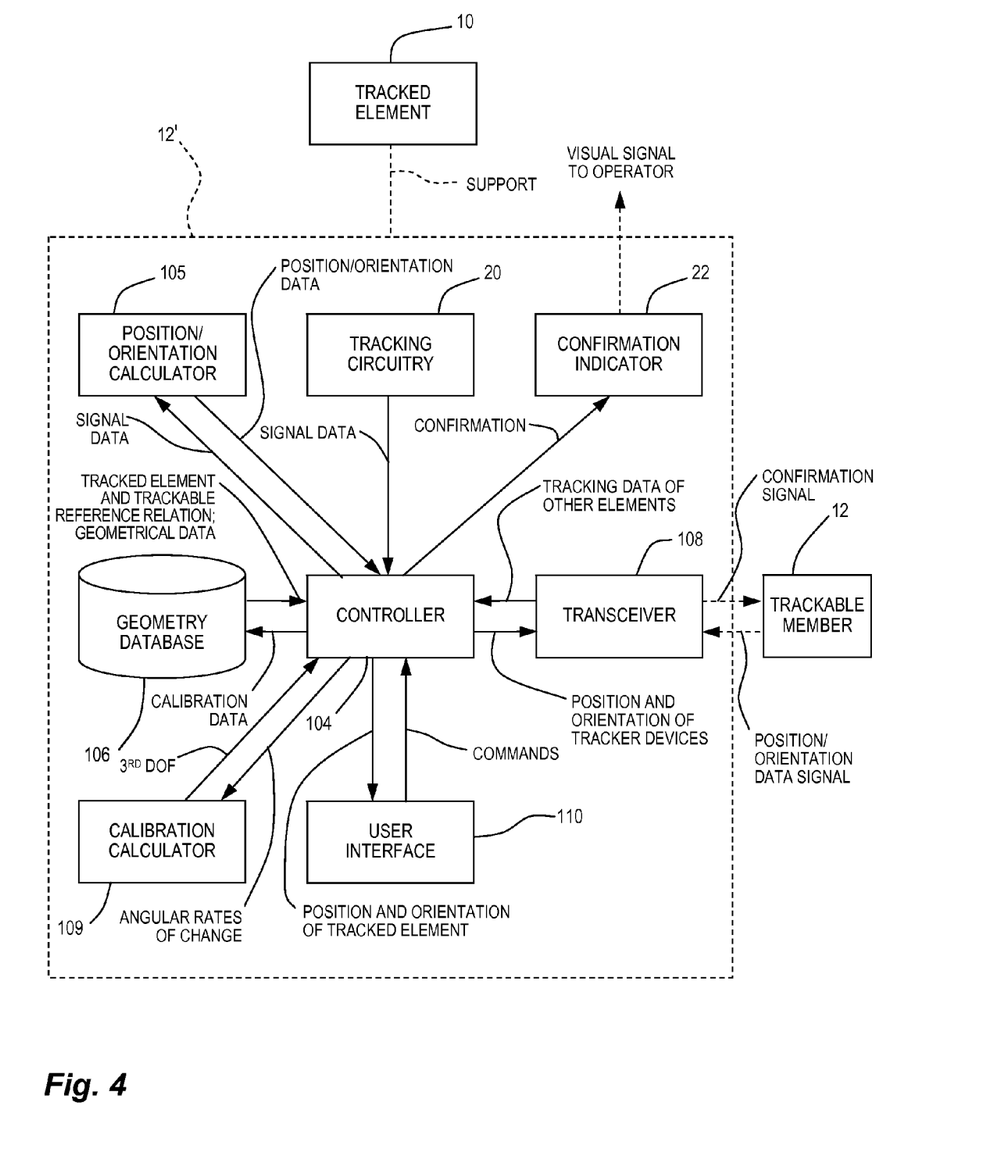
FIG. 4 is a block diagram of a self-enclosed tracking system in accordance with another embodiment of the present application, as used with a trackable member.

In the embodiments of FIGS. 3 and 4, at least two trackable members 12/12' are used in combination, with a first one of the trackable members 12' being secured to a bone or other bodily part, while a second one of the trackable members 12/12' is mounted to a tool/instrument, or to the bone for calibration. Therefore, any displacement of the bone is captured by the tracking circuitry 20 of its trackable member 12', which information is transmitted to the trackable member 12' on the tool/instrument. The tracking data is shared between the trackable members 12' such that the information provided on the user interface 110 represents the relative displacements between the bone and the tool/instrument.

In some instances, only the orientation (e.g., axes) between the bone and the instrument is required. In such a case, the tracking circuitry 21 of the trackable members 12' conveniently uses CAPAS.

Figure 5:
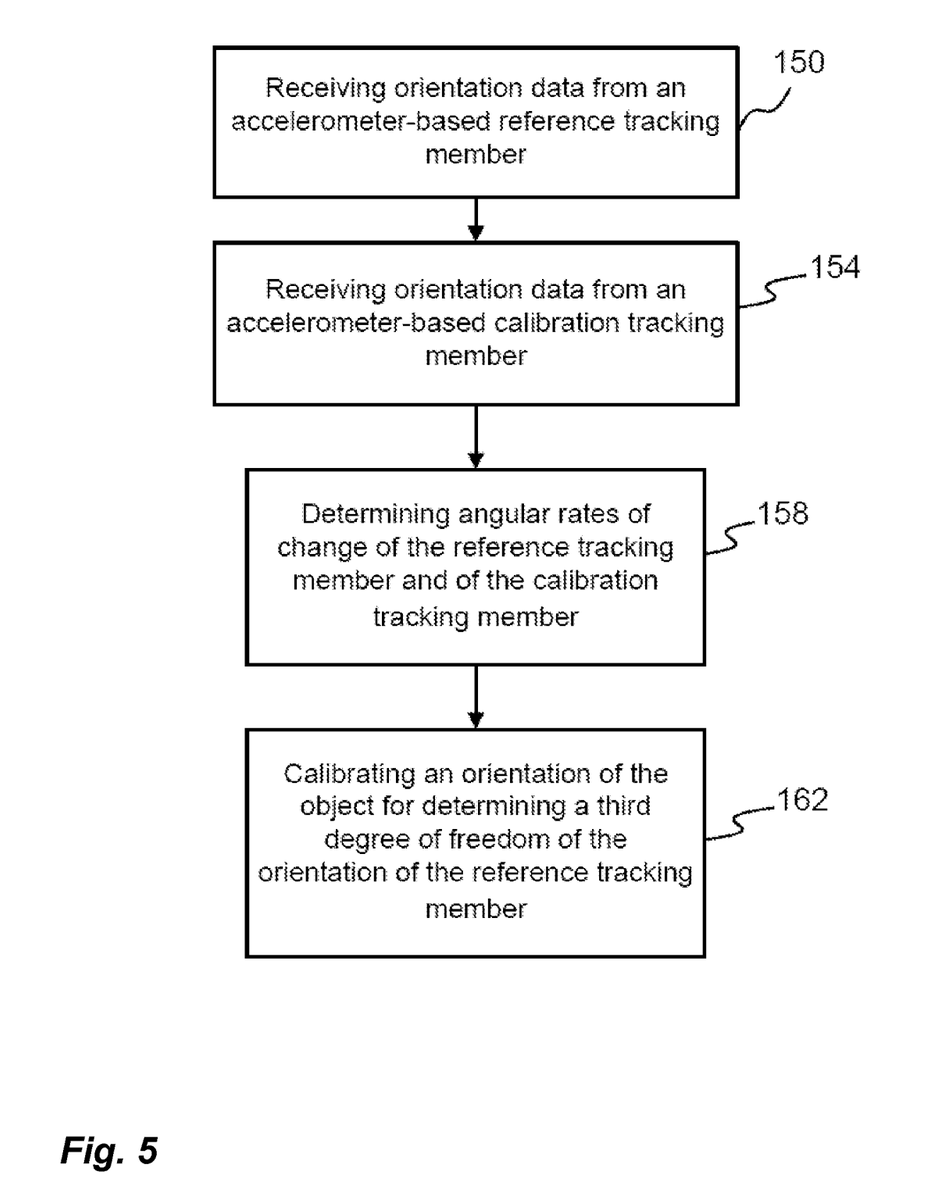
FIG. 5 is a flowchart illustrating a method for tracking three degrees of freedom of orientation of an object using the tracking system of FIGS. 3 and 4.

Referring to FIG. 5, a method is provided to calibrate a trackable member 12/12' having an accelerometer providing orientation data for 2 DOF in orientation, so as to provide a $3^{rd}$ DOF for the trackable member 12/12'.

As shown in FIGS. 3-5, the method comprises providing two of the trackable members 12/12' having accelerometers, and mounting both trackable members 12/12' to the object 10. One of the trackable members 12/12' is the reference tracking member, another is a calibration tracking member. Accordingly, the trackable members 12/12' both produce 2-DOF orientation data pertaining to the object.

According to 150 and 154, the orientation data from both trackable members 12/12' is received by the processing unit of the tracking system 100. The operator then performs motions of the object such that objects moves about one DOF of the trackable members 12/12'. For instance, the reference tracking member 12/12' is manually restricted in motion such that one orientation of the two DOFs does not vary while the other orientation of the two DOFs and the orientations of the two DOFs tracked by the calibration tracking member 12/12' vary.

According to 158, the processing unit of the tracking system 100 determines the angular rates of change of the reference tracking member 12/12' and of the calibration tracking member 12/12' while the object 10 rotates about an axis of only one of the two degrees of freedom of orientation of the reference tracking member, as mentioned above.

With these angular changes, the processing unit of the tracking system 100 can determine the $3^{rd}$ DOF of the reference tracking member 12/12'. Accordingly, at 162, the processing unit of the tracking system 100 calibrates an orientation of the object with reference to the reference tracking member 12/12' by using the determined angular rates of change, to determine the $3^{rd}$ degree of freedom of orientation of the reference tracking member 12/12'. With this calibration procedure, the object 10 is trackable in three degrees of freedom of orientation through the tracking data provided by the reference tracking member 12/12'.

The method involves defining a local coordinate system aligned with the gravity vector and one of the axes of the reference tracking member 12/12', constraining the $3^{rd}$ degree of freedom of the reference tracking member 12/12'. The orientation of the reference tracking member 12/12' and the calibration tracking member 12/12' can be expressed in this local coordinate system, before and after the constrained rotation mentioned above. This provides an fully-determined equation system with two unknowns corresponding to the $3^{rd}$ degree of freedom of the calibration tracking member 12/12' in the local coordinate system before and after the constrained rotation. Solving this equation system provides the full three degree of freedom of the calibration tracking member 12/12' relative to the reference tracking member 12/12'.

For the method of FIG. 5, it is preferred that the reference tracking member 12/12' and the calibration tracking member 12/12' are not in alignment for any axis of the two DOFs of orientation. Moreover, it is preferred to perform movements of greater amplitude for the object at 158, as their movements will result in greater values of angular rates of change. With greater angular rates of change, more precision may be attained in calibrating the $3^{rd}$ DOF.

Although it is preferred that there is no angular rate of change for the DOF associated with the axis of rotation of the reference tracking member 12/12', a small error may be accepted. During the gathering of data for calibration, the processing unit 101 may be programmed so as not to accept tracking data for the calibration when the angular change of the orientation of the axis of rotation is beyond a maximum threshold.

The invention claimed is:

1. A method for tracking three degrees of freedom of orientation of a bone during surgery, the method comprising:
   receiving angular orientation data having two rotational degrees of freedom of orientation from an accelerometer-based reference tracking member affixed to the bone;
   receiving angular orientation data having two rotational degrees of freedom of orientation from an accelerometer-based calibration tracking member affixed to the bone;
   determining angular rates of change of the reference tracking member and of the calibration tracking member while the bone is constrained to rotating about an axis of only one of the two rotational degrees of freedom of orientation of the reference tracking member; and
   calibrating an orientation of the bone with reference to the reference tracking member by using the determined angular rates of change to determine a third rotational degree of freedom of orientation of the reference tracking member;
   whereby the bone is trackable in three rotational degrees of freedom of orientation using only the angular orientation data produced by an accelerometer sensor of the reference tracking member.

2. The method according to claim 1, wherein determining angular rates of change of the reference tracking member and of the calibration tracking member comprises displaying data associated to an angular rate of change about the axis of the only one of the two rotational degrees of freedom of orientation of the reference tracking member, for guiding an operator in moving the bone.

3. The method according to claim 1, further comprising displaying a tracking of the bone in three rotational degrees of freedom of orientation on an interface after the calibrating.

4. The method according to claim 1, wherein determining angular rates of change comprises rejecting angular rates of change if an orientation about said axis varies beyond a maximum value.

5. A computer-assisted surgery system for tracking three degrees of freedom of an orientation of an bone, the computer-assisted surgery system comprising:
   an accelerometer-based reference tracking member adapted to be affixed to the bone, the reference tracking member producing angular orientation data for two rotational degrees of freedom of orientation by an accelerometer sensor thereof;
   an accelerometer-based calibration tracking member adapted to be affixed to the bone, the calibration tracking member producing angular orientation data for two rotational degrees of freedom of orientation by an accelerometer sensor thereof;
   a processing unit for receiving the angular orientation data from the reference tracking member and the calibration tracking member, the processing unit comprising:
      an orientation calculator for determining angular rates of change of the reference tracking member and the calibration tracking member while the bone is constrained to rotating about an axis of only one of the two rotational degrees of freedom of the reference tracking member; and
      a calibration calculator for calibrating an orientation of the bone with reference to the reference tracking member by using the determined angular rates of change to determine a third rotational degree of freedom of orientation of the reference tracking member whereby the bone is trackable in three rotational degrees of freedom of orientation using only the angular orientation data produced by an accelerometer sensor of the reference tracking member.

6. The computer-assisted surgery system according to claim 5, further comprising a user interface for displaying data associated with an angular rate of change about the axis of the only one of the two rotational degrees of freedom of orientation of the reference tracking member, for guiding an operator in moving the bone.

7. The computer-assisted surgery system according to claim 6, wherein the user interfaces displays a tracking of the bone in three rotational degrees of freedom of orientation on an interface after the calibrating.

8. The computer-assisted surgery system according to claim 5, wherein the processing unit rejects angular rates of change if an orientation about said axis varies beyond a maximum value.

* * * * *